United States Patent [19]
Kojiri et al.

[11] Patent Number: 5,437,996
[45] Date of Patent: Aug. 1, 1995

[54] MICROTETRASPORA STRAIN FOR PREPARATION OF INDOLOPYRROLOCARBAZOLE DERIVATIVES

[75] Inventors: Katsuhisa Kojiri; Hajime Suzuki; Hisao Kondo; Hiroyuki Suda, all of Tsukuba, Japan

[73] Assignee: Banyu Pharmaceutical Co., Ltd., Tokyo, Japan

[21] Appl. No.: 166,364

[22] Filed: Dec. 14, 1993

Related U.S. Application Data

[63] Continuation-in-part of Ser. No. 68,097, May 28, 1993, which is a continuation-in-part of Ser. No. 981,070, Nov. 24, 1992.

[30] Foreign Application Priority Data

Dec. 14, 1992 [JP] Japan .................................. 4-353623
Feb. 18, 1993 [JP] Japan .................................. 5-053035

[51] Int. Cl.$^6$ ............................................. C12N 1/20
[52] U.S. Cl. ...................................... 435/252.1; 439/119
[58] Field of Search ............................. 435/252.1, 119

[56] References Cited

U.S. PATENT DOCUMENTS 4,320,199  3/1982  Tomita ............................. 435/121

FOREIGN PATENT DOCUMENTS 0269025   6/1988   European Pat. Off. .
0445736   9/1991   European Pat. Off. .
9113071   9/1991   European Pat. Off. .
0450327  10/1991   European Pat. Off. .
9118003  11/1991   WIPO .

OTHER PUBLICATIONS

Tomita et al., J of Antibiot., vol. 44, 1991 pp. 940–948.
Kroppenstedt et al., In, "The Prokaryotes", ed. Balows et al, 1992 pp. 1085–1106.
Patent Abstract of Japan, JP-A 3-20277/1991, Banyu Pharmaceutical Co. Ltd.
Kojiri et al., "A New Antitumor Substance, BE-13793C, Produced by a Streptomycete", 44 Journal of Antibodies No. 7, Jul. 1991, pp. 723–728.
Hughes, et al., "Synthesis of the Indolo[2,3-a]carbazole Natural Products Staurosporinone and Arcyriaflavin B", J. Chemical Society Perkin Transactions, (1990), pp. 2475–2480.
Reynolds, et al., "The Preparation of α- and β-Geniobiose Octaacetates", 60 Journal of the American Chemical Society, Oct. 1988, pp. 2559–2561.

Primary Examiner—Irene Marx
Attorney, Agent, or Firm—Sherman and Shalloway

[57] ABSTRACT

The resultant compounds of the formula (I) have an excellent antitumor activity.

A process for preparation of a compound represented by the formula (I)

wherein
  $X^1$ and $X^2$ each independently represent hydrogen atom, halogen atom, amino group, mono- or di-lower alkylamino group, hydroxyl group, lower alkoxy group, aralkoxy group, carboxyl group, lower alkoxycarbonyl group, lower alkanoyloxy group or lower alkyl group, and
  R is hydrogen atom, amino group, formylamino group, lower alkanoylamino group, mono- or di- (Abstract continued on next page.)

lower alkylamino group, hydroxyl group, lower alkoxy group, aralkoxy group, aralkyl group or lower alkyl group, which comprises cultivating a microorganism having an ability to glycosylate a compound represented by the formula

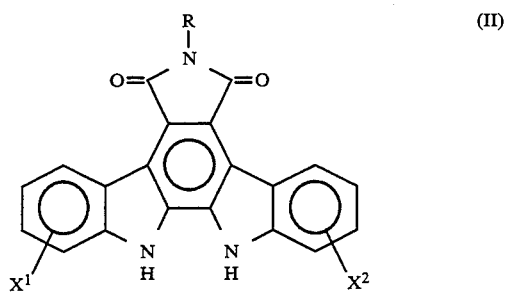

wherein $X^1$, $X^2$ and R have the same meanings as defined above, in a nutrient medium containing the compound of the above formula (II), and recovering the formed compound of the formula (I) from the culture medium.

1 Claim, No Drawings

MICROTETRASPORA STRAIN FOR PREPARATION OF INDOLOPYRROLOCARBAZOLE DERIVATIVES

This application is a Continuation-In-Part of Ser. No. 08/068,097, filed May 28, 1993, which is a Continuation-In-Part of Ser. No. 07/981,070 filed Nov. 24, 1992.

This invention relates to a novel process for preparation of indolopyrrolocarbazole derivatives, and, more detailedly, relates to a process for efficient preparation of indolopyrrolocarbazole derivatives having an antitumor activity by microbiological glycosylation.

The present inventors carried out investigation and research of antitumor substances, found a novel antitumor substance BE-13793 C (12,13-dihydro-1,11-dihydroxy-5H-indolo[2,3-a]pyrrolo[3,4-c]carbazole-5,7(6H)dione) in the metabolites of a microorganism, and disclosed it in Japanese Laid-Open Patent Publication KOKAI No. 20277/1991 and J. Antibiotics 44, 723-728 (1991).

Further, they produced indolopyrrolocarbazole derivatives represented by the formula

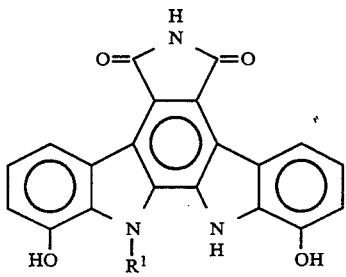

(A)

wherein R denotes a monosaecharide group having 5 to 7 carbon atoms, and the hydroxyl groups of this monosaccharide group can be replaced by the same or different 1 to 3 groups selected from the group consisting of a hydrogen atom, a lower alkyl group, lower alkylcarbonyloxy group and lower alkoxy group, which exhibit excellent antitumor activity, by introducing a glycosyl group at the 13-position of the above BE-13793C (see: PCT International Publication WO 91/18003).

They further carried out research, found that compounds obtained by introducing a glycosyl group at the 13-position of the indolopyrrolocarbazole derivatives and making various chemical modifications at the 6-position and represented by the formula

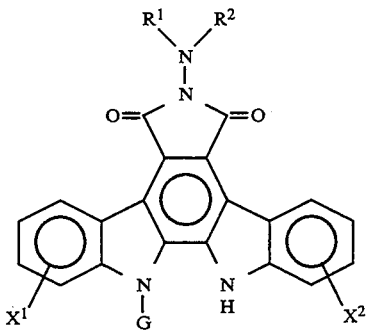

(B)

wherein $R^1$ and $R^2$ each independently represent a hydrogen atom, lower alkyl group, lower alkenyl group, lower alkynyl group, aryl group, aralkyl group or heterocyclic group (the lower alkyl group, lower alkenyl group, lower alkynyl group, aryl group, aralkyl group and heterocyclic group may each have 1 to 5 substituents selected from the group consisting of carboxyl groups, Carbamoyl groups, sulfo groups, amino groups, cyano groups, mono-lower alkylamino groups, di-lower alkylamino groups, hydroxyl groups and halogen atoms), or a group of the formula $-Y-R^3$, and therein Y represents a carbonyl group, thiocarbonyl group or sulfonyl group, and $R^3$ represents a hydrogen atom, lower alkyl group, cycloalkyl group, cycloalkylalkyl group, aryl group, aralkyl group, lower alkoxy group, hydrazino group, amino group, arylamino group, carbamoyl group or heterocyclic group (the lower alkyl group, cycloalkyl group, cycloalkylalkyl group, aryl group, aralkyl group and heterocyclic group may each have 1 to 4 substituents selected from the group consisting of halogen atoms, optionally protected hydroxyl groups, amino groups, carboxyl groups, carbamoyl groups, cyano groups and lower alkoxycarbonyl groups, and the amino group and carbamoyl group may each be mono- or di-substituted by lower alkyl group(s) optionally substituted by substituent(s) selected from the group consisting of halogen atoms, hydroxyl groups, amino groups, carboxyl groups, carbamoyl groups and lower alkoxycarbonyl groups); or $R^1$ and $R^2$ combine to represent a lower alkylidene group (the lower alkylidene group may have 1 to 4 substituents selected from the group consisting of amino groups, mono-lower alkylamino groups, di-lower alkylamino groups, hydroxyl groups, carboxyl groups and sulfonyl groups); or $R^1$ and $R^2$ combine together with the nitrogen atom to which they bind to form a heterocyclic group (the heterocyclic group may have on the ring lower alkyl group(s) optionally substituted by group(s) selected from the group consisting of amino groups, hydroxyl groups, carboxyl groups and sulfo groups), G represents a pentose group or hexose group, and $X^1$ and $X^2$ each independently represent a hydrogen atom, halogen atom, amino group, mono-lower alkylamino group, di-lower alkylamino group, hydroxyl group, lower alkoxy group, aralkoxy group, carboxyl group, lower alkoxycarbonyl group or lower alkyl group, have a further stronger antitumor activity, and disclosed them in EP-A-545195 (=U.S. patent application Ser. No. 07/981,070).

The object of this invention is to provide a process for smoothly and efficiently introducing a glycosyl group at the 13-position of indolopyrrolocarbazole derivatives.

The present inventors found that a microbiological glycosylation method is remarkably efficient for introduction of a glycosyl group into indolopyrrolocarbazole derivatives, and completed this invention.

Thus, this invention provides a process for preparation of a compound represented by the formula

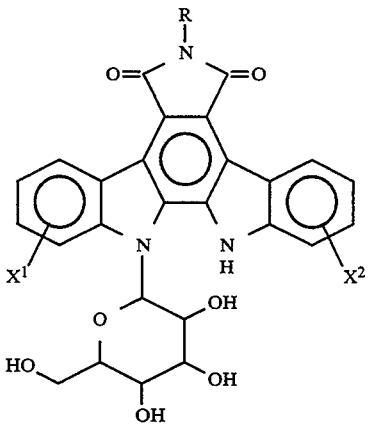

(I)

wherein $X^1$ and $X^2$ each independently represent hydrogen atom, halogen atom, amino group, mono- or di-lower alkylamino group, hydroxyl group, lower alkoxy group, aralkoxy group, carboxyl group, lower alkoxycarbonyl group, lower alkanoyloxy group or lower alkyl group, and R represents hydrogen atom, amino group, formylamino group, lower alkanoylamino group, mono- or di-lower alkylamino group, hydroxyl group, lower alkoxy group, aralkoxy group, aralkyl group or lower alkyl group, which comprises cultivating a microorganism having an ability to glycosylate a compound represented by the formula

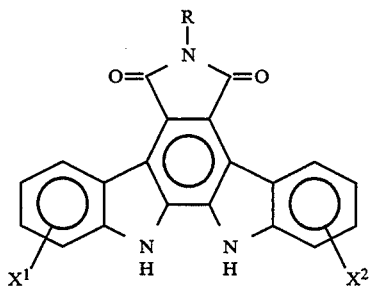

(II)

wherein $X^1$ $X^2$ and R are as defined above, in a nutrient medium containing the compound of the above formula (II), and recovering the formed compound of the formula (I) from the culture medium.

The process of this invention is described in more detail below.

The meanings of terms used in the present specification and claims are described below.

The term of "lower" means that the carbon number of a group or compound to which this term was attached is 6 or less. Therefore, a lower alkyl group means an alkyl group having 1 to 6 carbon atoms such as, for example, a methyl group, ethyl group, propyl group, isopropyl group, butyl group, isobutyl group, pentyl group, isopentyl group or hexyl group.

A lower alkanoyloxy group means an alkanoyloxy group having 2 to 6 carbon atoms such as, for example, an acetyloxy group, propionyloxy group, isopropionyloxy group, butanoyloxy group, isobutanoyloxy group, pentanoyloxy group, isopentanoyloxy or hexanoyloxy group.

A lower alkoxy group means an alkoxy group having 1 to 6 carbon atoms such as, for example, a methoxy group, ethoxy group, propoxy group, isopropoxy group, butoxy group, isobutoxy group, pentyloxy group, isopentyloxy or hexyloxy group.

A lower alkoxycarbonyl group means an alkoxycarbonyl group having 2 to 6 carbon atoms such as, for example, a methoxycarbonyl group, ethoxycarbonyl group, propoxycarbonyl group, isopropoxycarbonyl group, butoxycarbonyl group or pentoxycarbonyl group.

An aralkyl group means an aralkyl group having 7 to 12 carbon atoms such as, for example, a benzyl group, phenethyl group, phenylpropyl group, α-naphthylmethyl group, β-naphthylmethyl group, naphthylethyl group, or tetrahydronaphthylmethyl group.

An aralkoxy group means an aralkoxy group having 7 to 12 carbon atoms, such as, for example, a benzyloxy group, phenethyloxy group, phenylpropoxy group, α-naphthylmethoxy group, β-naphthylmethoxy group, naphthylethoxy group or tetrahydronaphthylmethoxy group.

A mono-lower alkylamino group means a monoalkylamino group having 1 to 6 carbon atoms such as, for example, a methylamino group, ethylamino group, propylamino group, isopropylamino group, butylamino group, isobutylamino group, pentylamino group, isopentylamino group or hexylamino group.

A di-lower alkylamino group means a dialkylamino group having on the nitrogen atom two alkyl groups each having 1 to 6 carbon atoms such as, for example, a dimethylamino group, diethylamino group, ethylpropylamino group, methylpropylamino group, butylethylamino group, methylpentylamino group or ethylhexylamino group.

An alkanoylamino group means an alkanoylamino group having 2 to 6 carbon atoms such as, for example, acetylamino group, propionylamino group, isopropionylamino group, butanoylamino group, isobutanoylamino group, pentanoylamino group, isopentanoylamino group or hexanoylamino group.

Halogen atoms mean a fluorine atom, a chlorine atom, a bromine atom and an iodine atom.

As a glycosyl group represented by the formula

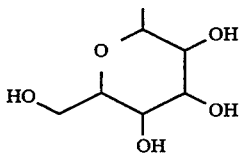

there can, for example, be mentioned an allose, altrose, glucose, mannose, gulose, idose, galactose or talose residue, and a glucose residue is particularly preferable.

This invention provides a process which comprises microbiologically glycosylating the compound of the formula (II) by using a microorganism to prepare the compound of the formula (I).

Any microorganism can be used in the above production process so long as it is a microorganism having an ability to glycosylate the compound of the formula (II) and for example, there can be used *Microtetraspora sp.* A 34549 strain, a kind of Actinomyces isolated from the soil of Yoro Keikoku, Ichihara-shi, Chiba-ken, *Saccharothrix aerocolonigenes* ATCC 39243 strain, or the like.

Bacteriological characteristics of *Microtetraspora sp.* A 34549 strain are shown below:

1. Morphological properties

The A 34549 strain does not form genuine aerial mycelia, and no spores are observed on the substrate mycelia. Further, division of mycelia is not observed, and specific organs such as sporangia and sclerotia are not observed.

2. Characteristics on culture on various agar plate media.

The results of culture at 28° C for 14 days in various agar plate media are shown in Table 1.

TABLE 1

| Medium | Growth | Aerial mycelium | Color of substrate mycelium | Soluble pigment |
|---|---|---|---|---|
| Yeast maltose agar (ISP-2) | good | trace | yellowish brown | brownish orange |
| Oatmeal agar (ISP-3) | good | not formed | grayish brown | none |
| Starch inorganic salt agar (ISP-4) | poor | not formed | colorless | none |
| Glycerol asparagine agar (ISP-5) | scarcely grow | | | |
| Peptone yeast iron agar (ISP-6) | good | not formed | yellowish brown | none |
| Tyrosine agar (ISP-7) | scarcely grow | | | |
| Nutrient agar | good | not formed | bright yellowish brown | light yellow |
| Sucrose nitrate agar | scarcely grow | | | |
| Glucose asparagine agar | scarcely grow | | | |

3- Growth temperature (yeast maltose agar medium, culture for 14 days)

Grows at 18° C. –43° C. and optimum growth temperature seems to be 30° C. or so.

4. Physiological properties

| | | |
|---|---|---|
| (1) | Liquefaction of gelatin (glucose peptone gelatin medium) | positive (weak) |
| (2) | Hydrolysis of starch (starch inorganic salt medium) | negative |
| (3) | Coagulation of skim milk powder (skim milk medium) | negative |
| (4) | Peptonization of skim milk powder (skim milk medium) | positive (weak) |
| (5) | Formation of melanoid pigment | negative |
| (6) | Common salt resistance (yeast maltose agar medium) | grows at common salt content of 2% or less |

5. Ability to utilize carbon sources

Culture was carried out at 28° C. for 14 days using Pridham-Gottlieb agar as a basal medium and adding the following various sugars. As a result, no growth was observed and judgment could not be made.

D-glucose, D-xylose, L-arabinose, L-rhamnose, D-fructose, D-galactose, raffinose, D-mannitol, inositol, salicin, sucrose 6. Cell components From the cell wall meso-diaminopimelic acid was detected but glycine, arabinose and galactose were not detected, and it was suggested that the type of the cell wall was type III. As the main sugar components of all the cells, madulose (arabinose, galactose and xylose are not contained) was detected, and its sugar pattern was type B, its phospholipid type was PIV and the main component of menaquinone was MK-9 (H4).

From the above microbiological properties, the A34549 strain was considered to belong to the genus Microtetraspora, an Actinomyces, and the A34549 strain was designated *Microtetraspora sp.* A34549.

This strain was deposited on Nov. 17, 1992 with the Fermentation Research Institute, Agency of Industrial Science & Technology, at 1–3, Higashi 1 chome Tsukuba-shi Ibaraki-ken 305 JAPAN, and the accession number is FERM P-13292, and after conversion to deposition under Budapest treaty as of February 25, 1993, FERM BP-4206.

A mutant of a microorganism having a glycosylating ability can be obtained by mutating a microorganism having an ability to glycosylate the compound represented by the formula (II) and to convert it to the compound represented by the formula (I), by a method usually used for a strain transformation treatment, for example, an irradiation treatment such as, e.g., X-ray or ultraviolet ray application; a treatment with a mutagen such as, e.g., nitrogen mustard, azaserine, nitrous acid, 2-aminopurine or N-methyl-N'-nitro-N-nitrosoguanidine (NTG); a phage contact transformation, transduction, conjugation, or the like.

A microbial strain used in the conversion of the compound of the formula (II) to the compound of the formula (I) is inoculated in a nutrient-containing medium and grown aerobically. As nutrient sources, those known as nutrient sources for microorganisms can be used. For example, as carbon sources, there can be used solely or as a mixture glucose, allose, altrose, mannose, gulose, idose, galactose, talose, glycerol, maltose, starch, sucrose, molasses, dextrin, etc. placed on the market. As nitrogen sources, there can be used solely or as a mixture soybean meal, corn gluten meal, corn steep liquor, meat extract, yeast extract, cotton seed meal, peptone, wheat germ, fish meal, inorganic ammonium salts, sodium nitrate, etc. placed on the market. As inorganic salts, there can be used calcium carbonate, sodium chloride, potassium chloride, magnesium sulfate, various phosphate salts, etc. Further, if necessary, salts of heavy metals such as iron, manganese, molybdenum, copper and zinc can be added in a trace quantity. Further, when there is too much foaming, there can appropriately, for example, be added as an antifoaming agent a vegetable oil such as soybean oil or linseed oil, a higher alcohol such as octadecanol, a silicone compound, or the like. Besides the above materials, there can be used any of materials utilized by the microorganism and useful for its growth such as, for example, 3-(N-morpholino) propanesulfonic acid or sodium borate.

As for a culture process, culture can be carried out in the same manner as in a general process for production of microbial metabolites except for addition of the compound of the formula (II) to a nutrient medium, and either solid culture or liquid culture can be adopted. In case of liquid culture, any of standing culture, stirring culture, shaking culture, aeration culture, etc. can be utilized, but shaking culture or submerged aeration stirring culture is preferable. Culture temperature is suitably 20° to 37° C., preferably 25° to 30° C. Preferred pH of a medium is in the range of 4 to 8, and a culture term is 2 to 20 days, preferably 7 to 15 days.

For recovery of the desired compound of the formula (I) from the culture medium, there can appropriately be utilized separation means usually used for recovery of metabolites produced by microorganisms from their culture media. Since the compound of the formula (I) exists in the culture filtrate or in the cells, it can be purified from the culture filtrate or the cells according to usual separation means such as, for example, solvent extraction method, ion exchange resin method, adsorption or partition chromatography, or gel filtration, either alone or in combination. Further, high performance liquid chromatography, thin layer chromatography or the like can also be utilized for extraction and purification.

In the process of this invention, a compound of the above formula (II) used as a starting compound can, for example, be prepared by either (A) reacting a compound represented by the formula

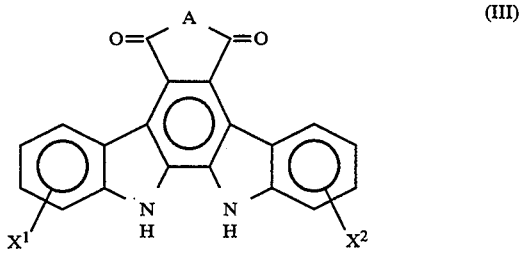

(III)

wherein

A represents oxygen atom or —NH—, and $X^1$ and $X^2$ are as defined above, or a derivative thereof wherein existing functional groups are protected, with a compound represented by the formula

$NH_2—R$ (IV)

wherein R is as defined above, or (B) reacting a compound of the above formula (III) or a derivative thereof wherein functional groups are protected, with hydrazine to form a compound of the formula (II) wherein R represents an amino group, and then formylating, lower alkanoylating, aralkylating or lower alkylating the amino group of this compound, or (C) reacting a compound of the above formula (III) or a derivative thereof wherein functional groups are protected, with hydroxylamine to form a compound of the formula (II) wherein R represents a hydroxy group, then aralkylating or lower alkylating the hydroxyl group of this compound, and, if necessary, removing the protective groups existing in the resultant compound.

Among the starting raw compounds of the above formula (III), compounds wherein A is —NH— can be prepared according to a process known per se, for example by a process utilizing the published method [refer to J. Org. Chem, 54, 824–828 (1989)]. Further, as an alternative process, these compounds can be prepared utilizing the indolocarbazole synthesis process disclosed in J. Chem. Soc. Perkin Transactions I, 2475–2480 (1990). Still further, it is also possible to utilize the synthetic process disclosed in Tetrahedron, 44, 2887–2892 (1988). On the other hand, among the strating raw compounds of the formula (III), compounds wherein A is an oxygen atom can be prepared according to the process disclosed in the later described Example C.

As the compounds of the formula (IV), commercial products can be used, or they can also be prepared by a known process.

The reaction of a compound of the formula (III) or a derivative thereof wherein functional groups are protected with a compound of the formula (IV), hydrazine or hydroxylamine can be carried out in the same manner as in the reaction of an imide or acid anhydride with hydrazine or a hydrazine derivative well known in the chemical field. In this reaction, it is possible to directly react without any solvent the compound of the formula (III) or the derivative thereof wherein functional groups are protected with the compound of the formula (IV), hydrazine or hydroxylamine, or it is also possible to use as a reaction solvent a solvent which does not have a bad influence on the reaction, for example tetrahydrofuran or the like.

There is no particular limitation about the amount of a compound of the formula (IV), hydrazine or hydroxylamine used in the reaction, and it is possible to carry out the reaction using it usually in an amount from a small excess to a large excess based on the compound of the formula (III) or the derivative thereof wherein functional groups are protected, but in the case of using no solvent it is preferable to use it in an excess amount of 10 to 40 moles.

Reaction temperature is usually in the range of about $-50°$ to about $50°$ C., but it is also possible, if necessary, to choose a temperature higher or lower than the temperature. Reaction time is usually in the range of about 30 minutes to about 2 days, but it is also possible, if necessary, to carry out the reaction in a time longer or shorter than the time.

Formylation of the amino group in compounds wherein R is an amino group among the thus obtainable compounds of the formula (II) can be carried out according to a process usually used for formylation of amino groups, and, for example, can be carried out according to a process which comprises heating such a compound with formic acid, formamide, dimethylformamide or the like, or a process which comprises reacting the amino group with a mixture of formic acid with an acid anhydride in a solvent which does not have a bad influence on the reaction or without an solvent.

The reaction of the amino group with formic acid, formamide, dimethylformamide or the like is usually carried out in the range of about 30° C. to the boiling point of the solvent, but, if necessary, can also be carried out at a temperature higher or lower than the temperature, and reaction time is usually in the range of 30 minutes to 2 days. In this occasion, it is preferable to carry out the reaction in the presence of an acid catalyst such as hydrochloric acid or sulfuric acid.

When the formylation is carried out using a mixture of formic acid with an acid anhydride, the formylation is usually carried out in the range of about $-5°$ C. to room temperature, but, if necessary, can also be carried out at a temperature higher or lower than the temperature. Reaction time is usually 10 minutes to 5 hours, but, if necessary, can be longer or shorter than the time.

Further, the lower alkanolyation of the above amino group can be carried out by a process which comprises reacting the amino group with a halide or arthydride of the corresponding lower alkanoic acid without any solvent or in an appropriate solvent, or the like. Reaction temperature is usually in the range of about $-5°$ C. to the boiling point of the solvent, but if necessary, can be a temperature lower than the temperature. The acid halide or acid anhydride is usually used in a small excess amount based on the compound of the formula (II) wherein R is an amino group, but, if necessary, can be used in an amount larger or smaller than that, and reaction time is usually about 30 minutes to about 2 days.

The alkylation of a compound of the formula (II) wherein R is an amino group can be carried out utilizing a process known per se for alkylation of an amino group, for example reaction with an alkyl halide, an alkyl mesylate or an alkyl tosylate or the like, condensation with an aldehyde compound or a ketone compound, followed by reduction reaction or the like.

Further, the aralkylation of a compound of the formula (II) wherein R is an amino group can be carried out utilizing the same process as in the alkylation reaction.

By the same process, it is possible to aralkylate or alkylate A of compounds wherein A is —NH— among the compounds of the above formula (III), and thereby compounds of the formula (III) wherein R is an aralkyl group or a lower alkyl group can be prepared.

Protection of the functional groups or removal of the protective groups can be carried out by usual processes widely known in the chemical field.

Further, the products of the above reactions can be purified according to methods known per se in the field of organic synthetic chemistry, for example a precipitation method, a solvent extraction method, recrystallization, chromatography, etc.

The compounds of the above formula (I) provided by the process of this invention have an excellent antitumor activity, as stated in WO 91/18003 and EP-A-545195, and are useful as an antitumor agent for control or prevention of diseases, particularly for treatment of cancers, or useful as a synthetic intermediate of indolopyrrolocarbazole derivatives having such antitumor activity.

This invention is more specifically illustrated by the following examples, but not limited only by these examples.

EXAMPLE A

A process for preparation of a compound represented by the following formula

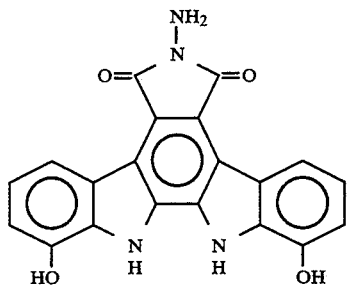

0.52 g of BE-13793C was dissolved in 3 ml of hydrazine hydrate (Wako pure chemical Co.) and stirred at room temperature for 1 hour. After acidifying the solution by conc. hydrochloric acid, resulting precipitates were collected by filtration and washed with water and then dried in vacuo. And thus 0.53 g of the compound represented by the above formula was obtained. (yield 98%)

Rf value: 0.63 (produced by Merck Co., Kiesel Gel 60 F$_{254}$, developing solvent: chloroform - methanol - tetrahydrofuran=3:1:1)

HPLC; Rt 19.1 minutes (column: Chromatorex ODS, inner diameter 4.6 mm, length 250 mm, detection: UV 305 nm, flow rate: 1 ml/min, mobile phase: 50% methanol to 100% methanol by linear gradient for 30 minutes)

FAB-MS (m/z) : 373 [M+H]$^+$ $^1$H-NMR (400 MHz, DMSO-d$_6$), δ(ppm): 11.6 (2H,s), 10.2 (2H,s), 8.44 (2H,d,J=7.8 Hz), 7.14 (2H,t,J=7.8 Hz), 6.98 (2H,d,J=7.8 Hz), 4.90 (2H,s)

EXAMPLE B

A process for preparation of a compound represented by the following formula

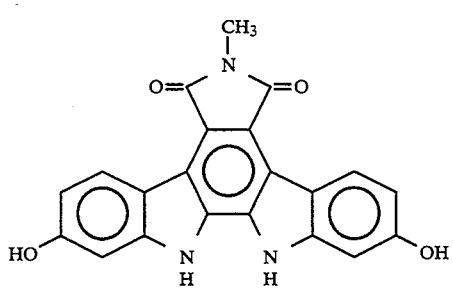

a) A solution of EtMgBr in THF (0.93 mol, 6.9 ml) was warmed up to 45° C. and 6-methoxyindole (949 mg) in Toluene (7.8 ml) was added. After 40 min, a solution of 2,3-dibromo-N-methylmaleimide (388 mg) in Toluene (7.8 ml) was added dropwise over 40 min, followed by refluxing for 2 hrs. The reaction mixture was ice-cooled and an aqueous 20% citric acid solution were added. The mixture was extracted with EtOAc and the organic extract was dried. The solvent was removed in vacuo and the residue was purified by chromatography or Sephadex LH-20 with MeOH to give 415 mg of 2,3-Bis-(6-methoxy-1H-indol-3-yl)-N-methylmaleimide (72%).

b) A solution of 410 mg of the compound obtained in step a) of Example B, 255 mg of 2,3-dichloro-5,6-dicyano-1,4-benzoquinone (DDQ) and catalytic amount of p-toluenesulfonic acid in 150 ml of dry benzene was refluxed for 45 min under Ar. The reaction mixture was cooled and sat. Na$_2$S$_2$O$_3$ were added. The mixture was extracted with EtOAc and the organic extract was washed with sat. NaHCO$_3$ and sat. brine. The solvent was removed in vacuo and the residue was purified by chromatography on silica gel, eluting with CHCl$_3$/MeOH/THF (30:1:1) and then CHCl$_3$-MeOH (10:1), yielding 250 mg of trimethylarcyriaflavin C (62%).

c) A mixture of 250 mg of the compound obtained in step b) of Example B, and 2.2 g of pyridine hydrochloride was heated to 180° C. in sealed tube for 1.5 h. The reaction mixture was cooled and diluted with DMF and 1N HCl. The mixture was extracted with EtOAc, and the organic phase was washed with H$_2$O and sat. brine. The solvent was removed in vacuo and the residue was purified by chromatography on Sephadex LH-20 with MeOH to give 131 mg of the compound represented by the above formula (6-methylarcyriaflavin C) (56%).

FAB-MS (m/z) : 372 [M+H]$^+$ $^1$H-NMR (300 MHz, DMSO-d$_6$), δ(ppm): 11.35 (2H,s), 9.73 (2H,s), 8.70 (2H,d,J=8.6 Hz), 7.04 (2H,d,J=2.0 Hz), 6.78 (2H,dd,J=8.6, 2.0 Hz), 3.14 (3H,s)

EXAMPLE C

A process for preparation of a compound represented by the following formula

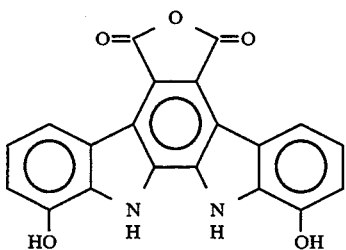

To 100 ml of 2N potassium hydroxide solution was added 1.2 g of BE-13793 C and stirred at room temperature for 5 hours. After adjusting the pH of the solution to 1.0 by addition of conc. hydrochloric acid, the resulting precipitates were collected by filtration and washed with 30 ml of water and then dried in vacuo. And thus 965 mg of the compound represented by above formula was obtained (yield 80%).

FAB-MS (m/z) : 359 [M+H]+

$^1$H-NMR (500 MHz, DMSO-d$_6$), δ(ppm): 11.9 (2H,brs), 10.4 (2H,brs), 8.24 (2H,d,J=7.8 Hz), 7.18 (2H,t,J=7.8 Hz), 7.01 (2H,d,J=7.8 Hz)

EXAMPLE 1

A process for preparation of 12,13-dihydro-1,11-dihydroxy-13-(5-D-glucopyranosyl)-5H-indolo[2,3-a]pyrrolo[3,4-c]carbazole-5,7(6H)dione The *Microtetraspora sp.* A 34549 strain cultured on a slant agar medium was inoculated in 100 ml of a medium (pH 7.2 before sterilization) containing 0.2% glucose, 2.0% dixtrin, 0.5% oatmeal, 0.5% defatted rice bran, 0.2% defatted meat bone meal, 0.1% dry yeast, 0.05% magnesium sulfate heptahydrate, 0.05% sodium bromide, 0.5% sodium chloride and 0.1% dipotassium hydrogen phosphate in a 500 -ml culturing Erlenmeyer flask, and cultured at 28° C. for 8 days on a rotary shaker (180 rpm). 2 ml of the culture broth was inoculated into 110 ml of a medium having the above composition in each of 20 culturing Erlenmeyer flasks having a capacity of 500 ml, and cultured at 28° C. on a rotary shaker (180 rpm). After culture for 9 days, 0.5 ml of a 20 mg/ml dimethylsulfoxide solution of BE-13793C was added per flask and culture was continued under the same conditions as above for further 15 days.

The resultant culture broths were extracted with 3L of methyl ethyl ketone (MEK). The resultant MEK extract was concentrated under reduced pressure. The resultant concentrate was extracted with ethyl acetate. The ethyl acetate extract (850 ml) was dehydrated with anhydrous sodium sulfate, and then concentrated to dryness. The residue was subjected to silica gel column chromatography (inner diameter 2 cm, length 30 cm, BW-350 silica gel, produced by Fuji Devison Chemical Co.), and after washing with chloroform - methanol - tetrahydrofuran - 28% aqueous ammonia (2:1:3:0.2), eluted with chloroform - methanol - tetrahydrofuran (3:1:1). The fraction containing the desired product was concentrated to dryness, the residue was dissolved in a small quantity of tetrahydrofuran - ethanol (1:3), subjected to Sephadex LH-20 column chromatography (inner diameter 1.5 cm, length 87 cm), and eluted with ethanol, and the fraction containing the desired product was concentrated to dryness to give 53.9 mg of the title compound, 12,13-dihydro-1,11-dihydroxy-13-(β-D-glucopyranosyl)-5H-indolo-2,3-a]pyrrolo[3,4-c ]carbazole-5,7(6H)-dione.

Rf value: 0.39 (produced by Merck Co., Kiesel Gel 60 F$_{254}$, developing solvent: chloroform - methanol - tetrahydrofuran - acetic acid=3:1:1:0.1)

HPLC; Rt 8.7 minutes (column:Chromatorex ODS, inner diameter 4.6 mm, length 250 mm, detection:UV 305 nm, flow rate:1 ml/min, mobile phase:methanol—water=6:4)

HR FAB-MS (m/z): 519. 1313

$^1$H-NMR (400 MHz, DMSO-d$_6$ ), δ(ppm): 11.0 (1H,s), 10.9 (1H,s), 10.3 (1H,brs), 9-93 ( 1H, brs), 8.69 (1H,d,J=7.8 Hz), 8.51 (1H,d ,J=7.8 Hz), 7-17 (2H,t,J=7.8Hz), 7.05 (1H,d,J=9.3 Hz), 7.01 (1H,d,J=7.8 Hz) , 6.9 (1H,d,J=7.8 Hz), 5.41 (1H,d,J=5.9 Hz), 5.34 (1H,brs), 5.20 (1H,d,J=5.4 Hz), 4.89 ( 1H,brs), 4.02 (2H,m), 3.74 (1H,m), 3.63 (2H,m), 3.41 (1H ,m)

EXAMPLE 2

A process for preparation of 12,13-dihydro-1,11-dihydroxy-13-(β-D-glucopyranosyl)-5H-indolo[2,3-a]pyrrolo[3,4-c]carbazole-5,7(6H)-dione The *Saccharothrix aerocolonigenes* ATCC 39243 strain cultured on a slant agar medium was inoculated in 110 ml of a medium (pH 7.2 before sterilization) containing 3.0% glucose, 1.0% soy flour, 1.0% pharma media and 0.3% calcium carbonate (Medium A) in each of seven 500-ml culturing Erlenmeyer flasks, and cultured at 28° C. for 48 hours on a rotary shaker (180 rpm). 4 ml of the culture broth was inoculated into 110 ml of a medium (pH 7.2 before sterilization) containing 1.0% glucose, 6.0% dextrin, 1.5% linseed meal, 0.5% autolyzed yeast, 0.1% ferrous sulfate heptahydrate, 0.1% ammonium dihydrogen phosphate, 0.1% ammonium sulfate and 1.0% calcium carbonate (Medium B) in each of 150 culturing Erlenmeyer flasks having a capacity of 500 ml, and cultured at 28° C. on a rotary shaker (180 rpm). After culture for 120 hours, 0.5 ml of a 22 mg/ml dimethylsulfoxide solution of BE-13793C was added per flask and culture was continued under the same conditions as above for further 120 hours.

The mycelium obtained by filtering the above culture broth were extracted with methanol (5.1 L and 5.6 L) and tetrahydrofuran (2.2 L and 2.3 L). The methanol and tetrahydrofuran extracts were combined and concentrated to about 1600 ml.

The aqueous concentrate was extracted with hexane (780 ml) to remove impurities and then extracted with ethyl acetate (3L). The ethyl acetate extract was concentrated to dryness.

The residue was washed with about 90 ml of ethyl acetate and extracted with about 90 ml of methanol. The methanol extract was concentrated to dryness to give 694 mg of yellowish orange solid.

This solid was dissolved in 40 ml of methanol, subjected to Sephadex LH-20 column chromatography (3.0×53 cm, produced by Pharmacia) and eluted with methanol. The fractions containing the desired product were combined and concentrated to dryness.

The residue was subjected to silica gel column chromatography (1.5×46 cm, Kiesel Gel 60, produced by Merck Co.), washed successively with chloroform and chloroform - methanol (10:1) and eluted with ethyl acetate - methanol (10:1). The eluent was concentrated to dryness to give 169 mg of the titled compound, 12,13-dihydro-1,11-dihydroxy-13-(β-D-glucopyranosyl)-5-H-indolo[2,3-a]-pyrrolo[3,4-c]carbazole-5,7(6H)-dione.

The physico-chemical properties of the obtained compound were identical with those of the compound obtained in Example 1.

EXAMPLE 3

A process for preparation of 6-amino-12,13-dihydro-1,11-dihydroxy-13-(β-D-glucopyranosyl)-5H-indolo[2,3-a]pyrrolo[3,4-c]carbazole-5,7(6H)-dione The *Saccharothrix aerocolonigenes* ATCC 39243 strain cultured on a slant agar medium was inoculated into a 500 ml flask containing 110 ml of Medium A described in Example 2 and cultured at 28° C. for 72 hours on a rotary shaker (180 rpm). 2 ml of the culture broth was inoculated into 8 of 500 ml flasks containing 110 ml of Medium B described in Example 2 and cultured at 28° C. for 120 hours on a rotary shaker (180 rpm).

Then, one ml each of tetrahydrofuran - methanol (3:7) solution containing 50 mg of 6-amino-12,13-dihydro-1,11-dihydroxy-5H-indolo[2,3-a]-pyrrolo[3,4-c]carbazole-5,7(6H)-dione was added to 8 flasks and cultivation was further continued for 96 hours under the same condition described above.

The mycelium obtained by filtration of the culture medium was extracted with 800 ml of tetrahydrofuran. Thus obtained 750 ml of extract was evaporated under reduced pressure and 500 ml of water was added and then extracted with ethyl acetate-n-butanol (10:1) solution 2 times. The organic layer was evaporated under reduced pressure and applied to silica gel chromatography (2.5×45 cm, Kiesel gel 60, Merck Co.). Elution was performed with chloroform - methanol - tetrahydrofuran - 25% ammonia water (2:1:3:0.2) and then with methanol - tetrahydrofuran - 25% ammonia water (1:3:0.2).

Purified eluate was evaporated under reduced pressure and the residue was dissolved with ethanol containing a small amount of tetrahydrofuran and then the solution was concentrated to yield 143 mg of the precipitates of the above title compound.

Rf value: 0.28 (produced by Merck Co., Kiesel Gel 60 F$_{254}$, developing solvent: chloroform - methanol - tetrahydrofuran=3:1:1)

HPLC; Rt 17.5 minutes (column: Chromatorex ODS, inner diameter 4.6 mm, length 250 mm, detection: UV 305 nm, flow rate: 1 ml/min, mobile phase: 50% methanol to 100% methanol by linear gradient for 30 minutes)

FAB-MS (m/z): 535 [M+H]$^+$ $^1$H-NMR (400 MHz, DMSO-d$_6$), δ(ppm): 10.9 (1H,s), 10.4 (1H,s), 10.0 (1H,s), 8.73 (1H,d,J=7.8 Hz), 8.55 (1H,d,J=7.8 Hz), 7.19 (2H,t,J=7.8 Hz), 7.05 (1H,d,J=9.3 Hz), 7.02 (1H,d,J=7.8 Hz), 6.90 (1H,d,J=7.8 Hz), 5.42 (1H,d,J=5.9 Hz), 5.34 (1H,brs), 5.22 (1H,brs), 4.96 (2H,brs), 4.91 (1H,d,J=4.9 Hz), 4.01 (2H,m), 3.74 (1H,m), 3.63 (2H,m), 3–39 (1H,m)

EXAMPLE 4

A process for preparation of 6-methyl-12,13-dihydro-2,10-dihydroxy-13-(β-D-glucopyranosyl)-5H-indolo[2,3-a]pyrrolo[3,4-c]carbazole-5,7(6H)-dione The *Saccharothrix aerocolonigenes* ATCC 39243 strain cultured on a slant agar medium was inoculated into a 500 ml flask containing 110 ml of Medium A described in Example 2 and cultured at 28° C. for 72 hours on a rotary shaker (180 rpm). 2 ml of the culture broth was inoculated into 2 of 500 ml flasks containing 110 ml of Medium B described in Example 2 and cultured at 28° C. for 120 hours or a rotary shaker (180 rpm). Then, one ml each of methanol solution containing 10 mg of 6-methyl-12,13-dihydro-2,10-dihydroxy-5H-indolo[2,3-a]pyrrolo-[3,4-c]carbazole-5,7(6H)-dione was added to 2 flasks and cultivation was further continued for 120 hours under the same condition described above.

The mycelium obtained by filtration of the culture medium was extracted with 100 ml of tetrahydrofuran 2 times. The obtained extracts were combined and evaporated under reduced pressure and 50 ml of water was added and then extracted with 50 ml of ethyl acetate 4 times. The organic layer was evaporated under reduced pressure and the residue was dissolved in ethanol and then applied to Sephadex LH-20 chromatography (1.5×90 cm, Pharmacia Co.). Elution was performed with ethanol and purified eluate was evaporated under reduced pressure to yield 11.1 mg of the title compound.

Rf value: 0.19 (produced by Merck Co., Kiesel gel 60 F$_{254}$, developing solvent: chloroform - methanol - tetrahydrofuran=3:1:1)

HPLC; Rt 20.0 minutes (column: Chromatorex ODS, inner diameter 4.6 mm, length 250 mm, detection: UV 305 nm, flow rate: 1 ml/min, mobile phase: 50% methanol to 100% methanol by linear gradient for 30 minutes)

H-NMR (400 MHz, DMSO-d$_6$), δ(ppm): 11.2 (1H,s), 9.76 (2H,brs), 8.88 (1H,d,J=8.3 Hz), 8.80 (1H,d,J=8.8 Hz), 7.18 (1H,d,J=2.0 Hz), 6.98 (1H,d,J=2.0 Hz), 6.83 (1H,dd,J=8.3, 2.0 Hz), 6.80 (1H,dd,J=8.8, 2.0 Hz), 5.98 (1H,d,J=8.8 Hz), 5.87 (1H,t,J=3.4 Hz), 5–35 (1H,d,J=4.9 Hz), 5.13 (1H,d,J=3.9 Hz), 4.95 (1H,d,J=4.4 Hz), 4.01 (1H,dd,J=10.7, 3.4 Hz), 3.91 (2H,m), 3–77 (1H,m), 3.51 (2H,m), 3.15 (3H,s)

We claim:
1. A biologically pure culture of *Microtetraspora sp.* A34549 (FERM BP-4206).

* * * * *